United States Patent [19]

Berger et al.

[11] 4,057,553

[45] Nov. 8, 1977

[54] CERTAIN PYRANO-FURO-AZULENO-PYRIDINES

[75] Inventors: Julius Berger, Passaic; Karen Emalyn Reichelt, Belleville, both of N.J.; Willy Schüep, Birsfelden, Switzerland

[73] Assignee: Hoffmann-La Roche Inc., Nutley, N.J.

[21] Appl. No.: 717,857

[22] Filed: Aug. 26, 1976

[51] Int. Cl.² .......................................... C07D 521/00
[52] U.S. Cl. ............................ 260/295 A; 260/297 F; 195/12; 195/109; 424/256
[58] Field of Search ........................ 260/297 F, 295 A

[56] References Cited

U.S. PATENT DOCUMENTS

| 3,894,029 | 7/1975 | Winterfeldt et al. | 260/295 A |
| 3,987,186 | 10/1976 | Devlin et al. | 260/295 A |

Primary Examiner—Alan L. Rotman
Attorney, Agent, or Firm—Samuel L. Welt; Bernard S. Leon; William H. Epstein

[57] ABSTRACT

Novel 1-propyl-3-methyl-azuleno[2,3-c]pyridine diones useful as coloring agents for foodstuffs, vitamins and pharmaceuticals and their method of preparation from Streptomyces Sp. X-14077 by fermentation.

14 Claims, No Drawings

CERTAIN PYRANO-FURO-AZULENO-PYRIDINES

SUMMARY OF THE INVENTION

In accordance with this invention it has been discovered that compounds of the tautomeric formulae

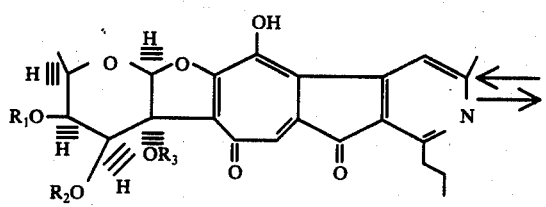

I-A

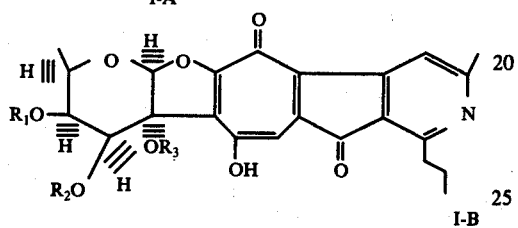

I-B wherein $R_1$ and $R_2$ are individually hydrogen or taken together form

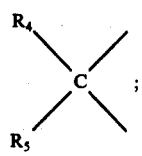

$R_3$ is hydrogen or

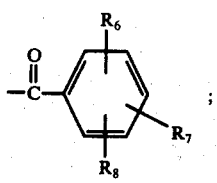

$R_4$ and $R_5$ are lower alkyl or form a cycloalkyl; and $R_6$, $R_7$ and $R_8$ are hydrogen, halogen or nitro are useful as coloring agents for foodstuff, vitamin, pharmaceutical and cosmetic compositions.

In accordance with another embodiment of the invention, compounds of the formulae

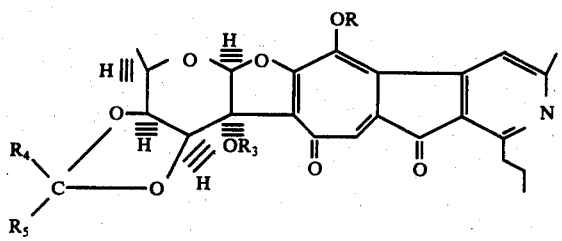

II-A and

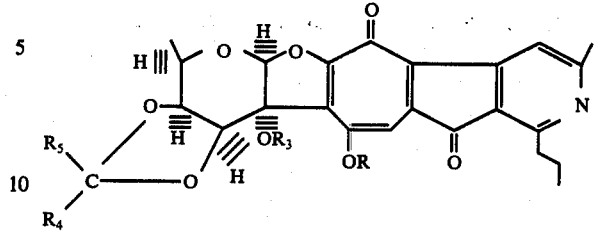

II-B wherein $R_3$, $R_4$ and $R_5$ are as above; and R is

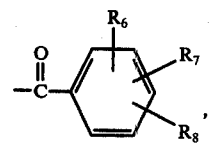

lower alkyl or

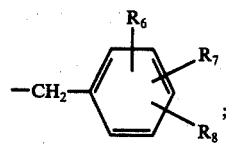

$R_6$, $R_7$ and $R_8$ are as above; with the proviso that when R is

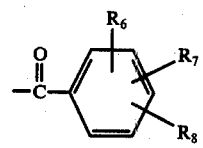

$R_3$ is other than hydrogen are useful as coloring agents for foodstuffs, pharmaceuticals, vitamins and cosmetic compositions.

In accordance with another embodiment of this invention, there is provided a coloring agent (coloring agent III) produced by cultivating a strain of Streptomyces Sp X-14077. This coloring agent is an amorphous red solid. While its exact structural formula is not known, it has a 1-propyl-3-methyl-azuleno[2,3-c]pyridine dione chromophore and its isopropylidene derivative has an empirical formula $C_{26}H_{27}NO_8$.

The compounds of tautomeric formulae I-A and I-B as well as the compounds of formulae II-A and II-B are produced from a compound of the tautomeric formulae I-A and I-B where $R_1$, $R_2$ and $R_3$ are hydrogen which is produced by the fermentation of Streptomyces Sp. X-14077. This fermentation also produces coloring agent III.

DETAILED DESCRIPTION OF THE INVENTION

The compounds of coloring agent III and of the tautomeric formulae

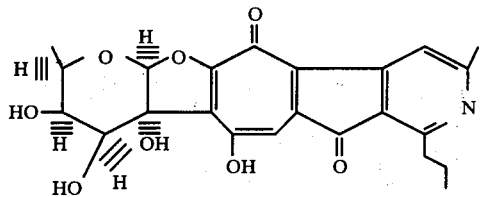

and

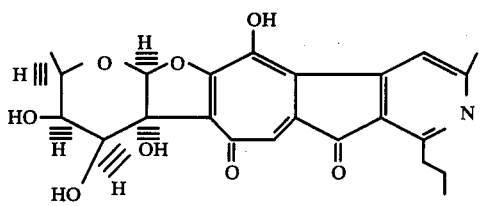

are prepared by cultivating a strain of *Streptomyces Sp.* X-14077 in an aqueous solution containing a nitrogen and carbon source under submerged aerobic conditions until substantial red color is imparted to said solution and then recovering said compounds from the solution.

The species *Streptomyces X*-14077 described herein includes all strains of Streptomyces which form the coloring agents and which cannot be definitely differentiated from the culture number X-14077 and its sub-cultures including mutants and variants.

The organism producing the coloring agent of the present invention was isolated from a sample of soil collected in eastern Argentina and is a new species designated *Streptomyces Sp. X*-14077. A culture of the living organism, given the laboratory designation X-14077 has been deposited in the Northern Regional Research Labs (NRRL), Peoria, Illinois and added to its permanent collection of microorganisms (NRRL 8144).

The representative strain of *Streptomyces Sp. X*-14077 has been characterized as follows.

The formulation of each medium used in the description of the growth characteristics is classified below.

DESCRIPTION OF CULTURE X-14077

The composition of the media used for cultivation and description of growth characteristics of this organism is given as follows:

Medium 1 ("Fermentation medium")

Bacto Thermoactinomyces fermentation broth (Difco) to which 1.5% of agar was added.

Medium 2 ("Tomato paste medium")

Dextose, 1%; $K_2HPO_4$, 0.1%; tomato paste, 2%; Protein partial hydrolysate (Medopeptone), 0.1%; $CaCO_3$, 0.2%; agar, 1.5% in tap water; pH, 6.8—7.3.

Medium 3 ("Glycerol-asparagine medium")

Glycerol, 1%, asparagine, 0.1%; $K_2HPO_4$, 0.1%; agar, 2% in tap water; pH, 7.0.

Medium 4 ("Starch-casein medium")

Soluble starch, 1%; casein, 0.1%; $K_2HPO_4$, 0.05%; $MgSO_4$, 0.05%; agar, 1.5%; pH, 7.4.

Medium 5 ("Bennett's medium")

Yeast extract, 0.1%; beef extract, 0.1%; N-Z Amine-A (casein hydrolysate), 0.2%; dextrose, 1%; agar, 1.8%; pH, 7.3.

Medium 6 ("Amidex medium")

Starch preparation (Amidex, Corn Products Co.), 1%; N-Z Amine-A, 0.2%; beef extract, 0.1%; yeast extract, 0.1%; $CaCl_2$: $2H_2O$, 0.0014%; agar, 2%; pH, 7.3.

Media 7, 8, 9 and 10 are, respectively, media 2, 3, 4 and 5 described by Shirling, E. G., and Gottlieb, D., Methods for characterization of *Streptomyces* species, International J. of Systematic Bacteriol. 16:313-340, 1966.

Medium 11 ("Sporulation medium" as recommended by ATCC)

Yeast extract, 0.1%; beef extract, 0.1%; tryptose, 0.2%; $FeSO_4$, trace; glucose, 1%; agar, 1.5%.

Unless otherwise indicated, the observations reported were performed after an incubation period of 14 days at 28° C.

The morphological features of culture X-14077 are the following: On Medium 3, after an incubation period of 11 to 14 days at 28° C., there is abundant aerial growth with hyphae of medium length; the filaments are frequently branched, and there is abundant production of sporophores mostly coiled in spirals, hooks and loops. The characteristics of the aerial growth are essentially the same on media 2 and 4, although on medium 2, many primitive spirals (along with well formed ones) are also observed. According to the aerial type of growth this strain can be placed in the category *retinaculum-apertum* (RA).

The spore chains have more than 10 spores each (generally from 10 to less than 50); the spores are globose (from 1.1 to 1.5 μm by 1.2 to 1.4 μm) and their surface is spiny. The L,L isomer of diamino-pimelic acid is found in the composition of this organism. This, taken together with the morphological traits mentioned above, place it in the genus *Streptomyces*.

Type of growth, aerial mycelium, color of upper surface and reverse of colonies, and the pigment excreted into the medium for various culture media, are summarized in Table I below. In this Table, the description of colors is according to the Color Harmony Manual (Container Corp. of America); Fourth Edition, 1958.

TABLE I

| Medium | Characteristics of the aerial growth | Color of upper surface of colonies | Color reverse of colonies |
|---|---|---|---|
| 1 | abundant, raised, wrinkled surface, slightly biting edges; good sporulation; redwood pigment excreted into medium | natural (2 dc) to convert gray (2 fe) | hard to determine, due to density of pigment excreted by culture |
| 2 | abundant; center of colonies raised; barn red pigment; partial sporulation (about 50% of aerial surface) | cloud pink (7 cb) to dawn pink (7 dc) to pussywillow gray (5 dc) | same as for medium 1 |
| 3 | abundant; center of colonies raised; leathery; partial sporula- | natural (3 dc) to silver gray (3 fe) or ashes gray (5 fe) | same as for medium 1 |

TABLE I-continued

| Medium | Characteristics of the aerial growth | Color of upper surface of colonies | Color reverse of colonies |
|---|---|---|---|
| | tion; coral rose pigment excreted. | | |
| 4 | abundant; colonies very slightly raised, with smooth edges; good sporulation; frequent sectoring of colonies; brick red pigment excreted into medium | natural (4 dc) to ashes (5 fe) | same as for medium 1 |
| 5 | abundant; colonies raised and somewhat wrinkled; slightly biting edges; agar cracked; partial sporulation (about 30% of surface); redwood pigment excreted | natural (3 dc) to silver gray (3 fe) | cork tan (4 ie) to dark brown (4 pn) |
| 6 | abundant; wrinkled; coarse surface; biting edges; partial sporulation; brick red pigment excreted | sand gray (3 cd) to cloud pink gray (7 cb) | same as for medium 1 |
| 7 | abundant; colonies raised, very coarse surface, biting; good sporulation; red mahogany pigment excreted | olive gray (1 ih) with white specks to silver gray (3 fe), to pearl (3 ba) | same as for medium 1 |
| 8 | abundant; flat colonies, of finely coarse surface, with good sporulation; rose wine pigment excreted | olive gray (1 ih) to natural (3 dc) | old rose (7 ie) |
| 9 | abundant; raised colonies with finely coarse surface, slightly biting edges; good sporulation; brick red pigment excreted | olive gray (1 ih) | same as for medium 1 |
| 10 | fair; slightly raised colonies; very finely granular surface; very poor sporulation; pale pink pigment excreted | non-sporulated areas pink (6 ½ ea) | red mahogany (6 ½ pi) |
| 11 | abundant; wrinkled; edges of colonies biting; partial sporulation; cedar redwood pigment excreted | natural (3 dc) | same as for medium 1 |

Growth of the organism was observed at three temperatures, namely, 28°, 35° and 50° C. This last is probably close to the maximum growth temperature because very little growth, if any, occurs above 50° C. Growth is also doubtful at 10° C. Pigment production is best at temperatures where growth is faster, namely between 28° and 35° C. Sporulation is somewhat better at 35° than at 28° C. A limited number of carbon assimilation tests has shown that this organism grows very well at the expense of glucose, fructose and galactose; growth on L-arabinose, sucrose, xylose and mannitol is poor. There is no growth with m-inositol, rhamnose, raffinose, cellulose, or salicin.

Streptomyces X-14077 when grown under suitable conditions, produces the compounds of formula IV-A and IV-B as well as coloring agent III. A fermentation broth containing Streptomyces X-14077 is prepared by inoculating or mycelia of this organism into a suitable medium and then cultivating this medium under aerobic conditions. For the production of a compound of the formula I, cultivation on a solid medium is possible but for production in large quantities, cultivation in the liquid medium is preferable. The temperature of cultivation can vary over a wide range, i.e., from 20° C to 40° C, within which the organism can grow but a temperature of 26° C to 30° C in a substantially neutral pH is preferred, i.e. from 6 to 9 with 7.2 to 8 being especially preferred. In the submerged aerobic fermentation of the organism for the production of a compound of the formula I, the medium may contain any suitable carbon source. Among the preferred suitable carbon sources are included commercially available glyceride oil or a carbohydrate such as glycerol, glucose, mannitol, maltose, lactose, dextrin, starch, etc, in pure or cured states. Furthermore, the medium should contain a source of nitrogen. Any conventional nitrogen source can be utilized in the medium in accordance with this invention. Among the preferred nitrogen sources are organic materials such as soybean meal, distillers' solubles, peanut meal, cotton seed meal, meat extract, peptone, fish meal, yeast extract, corn steep liquor, etc, and, when desired, inorganic sources of nitrogen such as nitrates and ammonium salts and mineral salts such as ammonium sulfate, magnesium sulfate and the like. The medium may also contain inorganic salts such as sodium chloride, potassium chloride, potassium phosphate and the like; buffering agents such as sodium citrate, calcium carbonate or phosphates as well as trace elements, i.e. trace amounts of heavy metal salts. In aerated submerged culturing procedures, an anti-foam agent such as liquid paraffin, fatty oils or silicon compounds is used. More than one kind of carbon source, nitrogen source, or anti-foam source may be used in the production of the coloring agent of tautomeric formulae IV-A and IV-B as well as coloring agent III.

In carrying out the fermentation, any conventional method of aerobic fermentation under the conditions of temperature and pH designated above can be utilized. The fermentation can be carried out under these submerged aerobic conditions for a period of time of at least until red color is imparted to the aqueous solution.

In general, the production of the coloring agents of tautomeric formulae IV-A and IV-B as well as coloring agent III by submerged aerobic fermentation occurs within one day. However, if desired, fermentation can be carried out for periods of up to 10 days or longer, generally it is preferred to carry out the fermentation for a period of from 1 to 5 days. If desired, fermentation periods of greater than 10 days can be utilized. However, in view of the fact that no additional beneficial results are achieved by utilizing such long fermentation times, these long fermentation times are seldom utilized.

As indicated above, the aforementioned coloring agents are prepared under submerged aerobic conditions. Submerged fermentation preferably results in the production of a large quantity of the coloring agents in accordance with conventional procedures.

Following its production under submerged aerobic conditions, the coloring agent can be recovered from the fermentation broth by methods commonly employed in the fermentation art. Thus, for example, mycelia and undissolved solids can be removed from the fermentation broth by conventional means such as filtration and centrifugation. The coloring agents can be recovered from the filtered broth by conventional isolation techniques such as adsorption or solvent extraction.

The coloring agent III can be separated from the compound of tautomeric formulae IV-A and IV-B by any conventional method of separation such as chromatography or resin adsorption. Any of the conventional techniques utilized in resin adsorption or chromatography can be utilized to separate the coloring agents.

Coloring agent III is a red amorphous solid. While its structural formula has not been determined, it contains the 1-propyl-3-methyl-azuleno[2,3-c] pyridine dione chromophore, i.e.,

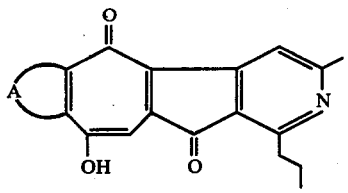

and its tautomeric form. Furthermore, the isopropylidene derivative of coloring agent III formed under conventional conditions utilizing ketalized acetone has the empirical formula $C_{26}H_{27}NO_8$. The formation of this derivative is carried out utilizing any conventional method of ketalizing acetone with a dihydroxy compound. Generally this reaction is carried out in the presence of a strong acid such as an inorganic acid. Among the preferred inorganic acids are the hydrohalic acids such as hydrochloric acid, etc., as well as sulfuric acid. In carrying out this reaction, temperature and pressure are not critical and room temperature and atmospheric pressure can be utilized. However, higher temperatures such as reflux are preferred.

The NMR spectrum and UV data with respect to coloring agent III are as follows:

$\lambda_{max}^{H_2O}$ (ε) 218 (18000), 273 (21300), 333 (8600), 412 (6700), 520 (5200) nm; ir (KBr) 3400 (broad), 1720, 1650, 1590, 1580 cm$^{-1}$.

The compound of tautomeric formulae IV-A and IV-B can be converted to the compound of tautomeric formulae I-A and I-B where $R_3$ is hydrogen and $R_1$ and $R_2$ form

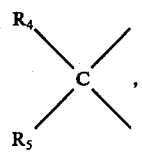

i.e., the ketal, by reacting the compound of formulae I-A and I-B with a ketone of the formula

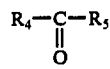

wherein $R_4$ and $R_5$ are as above. This reaction is carried out in the same manner as described hereinbefore in connection with the formation of the isopropylidene derivative of the coloring agent of formula III. This ketal is converted to the compound of tautomeric formulae I-A and I-B wherein $R_3$ is

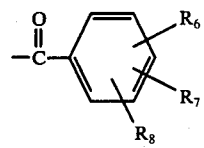

i.e., the ester ketal, by reacting this ketal with a reactive derivative of an acid of the formula

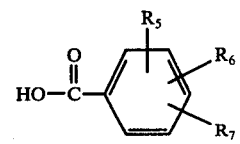

wherein $R_5$, $R_6$ and $R_7$ are as above. Among the reactive derivatives of the compounds of formula XI are included the acid halides, anhydrides, etc. Any conventional reactive derivatives of an organic acid that will react with a hydroxy group to produce an ester can be utilized to carry out this reaction. This reaction is carried out by conventional esterification reaction. When one mole of the reactive derivative of the compound of formula XI is utilized per mole of the ketal of tautomeric formulae I-A and I-B the compound of tautomeric formulae I-A and I-B is produced where $R_1$ and $R_2$ form the cyclic ketal and $R_3$ is

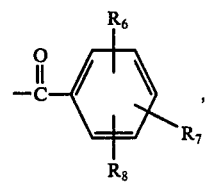

i.e., the ketal ester of tautomeric formulae I-A and I-B. On the other hand, when two moles of the compound of formula XI are used to esterify the ketal of tautomeric formulae I-A and I-B, the compounds of formulae II-A and II-B where both R and $R_3$ are

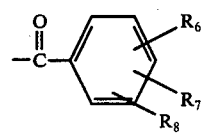

are produced as a mixture. This mixture can be separated by any conventional method such as chromatography; etc. Any conventional method of chromatography can be utilized to separate the compound of formula II-A from the compound of formula II-B.

The compound of tautomeric formulae I-A and I-B where $R_1$ and $R_2$ form a cyclic ketal and $R_3$ is

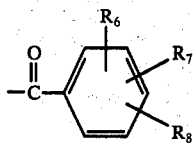

can be converted to the corresponding compounds of tautomeric formulae I-A and I-B where $R_1$ and $R_2$ are hydrogen by conventional ketal cleavage. Any conventional method of ketal cleavage can be utilized to effect this reaction. This ketal cleavage will not affect the ester group formed by $R_3$ since it remains protected during this cleavage due to the fact it is an ester of a tertiary hydroxy group.

The compounds of formulae II-A and II-B where R is

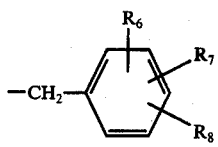

or lower alkyl, i.e., the ether ketal, are formed by treating the compounds of the tautomeric formulae I-A and I-B where $R_1$ and $R_2$ form a cyclic ketal with a reactive derivative of a lower alkanol or a benzyl alcohol of the formula

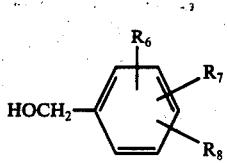

wherein $R_6$, $R_7$ and $R_8$ are as above. Any conventional reactive derivative of an alcohol can be utilized to produce the ether derivative of formula II-A or II-B. Among the reactive derivatives are the halides. Any conventional method of etherification can be utilized to form the ketal ethers of formulae II-A and II-B. Etherification with a reactive alcohol derivative produces the compounds of formula II-A and II-B as a mixture. This mixture can be separated by conventional means such as chromatography.

The term "halogen" as used throughout this application designates all four halogens, i.e., chlorine, bromine, fluorine and iodine. The term "lower alkyl" designates both branched and straight chain lower alkyl groups containing from 1 to 6 carbon atoms such as methyl, ethyl, n-propyl, isopropyl, etc., with straight chain lower alkyl groups being preferred. When $R_4$ and $R_5$ are taken together with their attached carbon atom, they can form a cycloalkyl ring structure. The term cycloalkyl as used herein denotes cycloalkyl groups which contain from 3 to 8 carbon atoms, i.e. cyclopropyl, cyclobutyl, cyclohexyl, with cyclohexyl being especially preferred.

The coloring agents of the tautomeric formulae I-A and I-B as well as the formulae II-A and II-B and coloring agent III above, in accordance with this invention, can be used to color any conventional foodstuff which includes beverages such as fruit drinks, soda pop, etc., gelatin, fruits, gum, candy, vegetable preserves, marmalades, cream foods, confectionary, edible fats, yellow cheese, fish products, pasta, soup powders, carbonated beverages, etc. Any conventional pharmaceutical preparation can be colored by these compounds. Among the typical pharmaceutical preparations which can be colored in accordance with this invention are included dragees, suppositories, gelatin capsules and syrups. Also any conventional cosmetic preparations can be colored with these compounds. Among the conventional cosmetic preparations which can be colored in accordance with this invention are included toothpaste, face creams, lipsticks and non-alcoholic mouthwashes.

In coloring materials such as foodstuffs, cosmetic and pharmaceutical preparations, the compounds of the tautomeric formulae I-A and I-B as well as the formulae II-A and II-B and coloring agent III above should be added to the material in an amount sufficient to impart a color to the material. Generally, it is preferred that the foodstuff, pharmaceutical and cosmetic preparation contain from about 0.001 parts by weight to about 5 parts by weight of the compound of formula I above based on the weight of the foodstuff, pharmaceutical and cosmetic preparation. It is suitable to make the amount of the coloring agent to be added dependent on the nature of the preparations to be colored and the amount of color desired.

The coloring agents of this invention can be employed for coloring foodstuffs, pharmaceutical and cosmetic preparations both in the original solid form or dissolved in an aqueous solution. The coloring agents of this invention are extremely advantageous since they are water soluble and can be simply mixed with the material to be colored or be applied to the material to be colored as an aqueous solution.

The coloring agents of this invention can be incorporated in the material to be colored alone or as a mixture. Among the preferred coloring agents is a mixture of the compound of tautomeric formulae IV-A and IV-B with coloring agent III. Therefore, the product of the fermentation of Streptomyces Sp. X-14077 (NRRL 8144) after separating from the fermentation broth by conventional means such as filtration is a coloring agent composed of a compound of the tautomeric formulae IV-A and IV-B and coloring agent III. This solid mixture can be used without separation to color foodstuffs, pharmaceutical and cosmetic preparations.

The following examples are illustrative but not limitative of the invention. In the examples, all temperatures are in degrees Centigrade and the Streptomyces Sp. X-14077 was Streptomyces Sp. X-14077 (NRRL 8144).

In the Example 1, Bacto Thermoactinomyces fermentation broth had the following composition (9% by weight)

0.5% N.Z. amine B
0.2% Difco Yeast Extract
0.2% Soy Protein-enzyme hydrolysate (Bacto-Soytone, Difco)
1.0% Soluble Starch
0.5% D-Mannitol
1 ml tract elements solution, 1 liter broth The trace elements solution utilized above and in Examples 1 and 3 were

|  | g/liter |
|---|---|
| $FeSO_4 \cdot 7 H_2O$ | 7.5 |
| $Fe(NH_4)_2(SO_4)_2$ | 7.02 |
| $ZnSO_4 \cdot 7H_2O$ | 4.4 |

| | g/liter |
|---|---|
| $MnSO_4 \cdot H_2O$ | 1.54 |
| $CuSO_4 \cdot 5H_2O$ | 0.314 |
| $CoCl_2 \cdot 6H_2O$ | 0.404 |
| $H_3BO_3$ | 0.572 |
| $H_2O$ | To Volume |

EXAMPLE 1

*Streptomyces sp.* X-14077 was maintained on stock slants of agar for 5–8 days, by which time sporulation was abundant. A slant was macerated with distilled water to provide fluid inoculum for inoculation of a 500 ml Erlenmeyer flask containing 75 ml of Bacto Thermoactinomyces fermentation broth. The flask was incubated for 3 days at 28° C on a rotary shaker at 240 RPM, by which time growth was heavy.

About 75 ml of this inoculum was combined with material prepared by blending in a high speed blender the contents (~ 20 ml) of an agar plate, which had been streaked 3 days earlier with a mycelial suspension from a benchscale fermentation. The blend was then resuspended to a total of 200 ml with the medium. This combined inoculum was used to seed 12 liters of sterile medium of the following composition (% by weight):

0.5% N.Z amine B [Enzyme hydrolysate of animal and milk protein]
0.2% Difco Yeast Extract
0.2% Soy Protein Enzyme hydrolysate (Bacto-Soytone, Difco)
1.0% Corn Starch (dextrin)
0.5% D-Mannitol
1 ml of trace elements solution/liter of broth
0.01% antifoam
pH 7.2 ± 0.2

This composition was contained in a 14 liter fermentor. Incubation was at 28° C, with aeration at 4 liters per minute, agitation at 1250 RPM, and at atmospheric pressure. The pH varied from 7.2 initially to 7.6 at harvest. Incubation was for 70 hours at which time 11 liters of well developed growth were transferred to 225 liters of sterile medium of the composition given above contained in a 400 liter stainless steel fermentor. This medium was sterilized 30 minutes at 120° C. The fermentor was operated at 28° C and 350 RPM. For the first 42 hours, the air flow rate was 110 liters per minute and the fermentor was at atmospheric pressure. For the remainder of the run the air flow was at 70 liters per minute and the fermentor pressure was 5 psig. The broth was harvested at 67 hours while the yield was still increasing.

At harvest, 10 pounds of diatomaceous earth (Hyflo) were added, and the broth was centrifugally filtered on a 40 inch perforated basket centrifuge using a coarse canvas bag and a Hyflo precoat. Approximately 15–20 liters of broth from two similar, simultaneously-run stirred jar fermentations were pooled with the brothHyflo mixture before filtration. Two hundred fifty liters of filtrate were recovered. The filtrate was estimated to contain 160 mg/liter of the dione 8(R), 9(R), 10(S), 10a(R)-tetrahydro-9,10,10a,11-tetrahydroxy-3,8-dimethyl-1-propyl-6aH(S)-pyrano[2″, 3″:5′,6′]furo[2′,3′:5,6]azuleno-[2,3-c]pyridine-5,13-dione by assay. The filtrate thus contained a total of about 40 grams of the dione.

The filtrate was extracted three times, each time with 190 liter portions of n-butanol. The first butanol extract was estimated to contain 150 mg of the dione/liter, the second extract 40 mg/l, and the third extract 14 mg/l. The emulsion formed with each extraction was broken by passage through a centrifuge.

Five hundred sixty liters of butanol extract were pooled and assayed at 70 mg/l, for a total of 39.2 grams of the dione. The recovery from the filtrate by extraction was, therefore, 98%.

The pooled extracts were concentrated under reduced pressure at less than 50° C using a wiped film evaporator. Eleven liters of concentrate containing 2.53 g dione/liter were recovered, for a total of 27.8 grams of the dione. The overall recovery at this point was 70 percent.

EXAMPLE 2

The medium utilized in this example was as follows:
0.5% N.Z. amine B
0.2% Difco Yeast Extract
0.2% Soy protein enzyme hydrolysate (Bacto-Soytone, Difco)
1.0% soluble starch
0.5% D-Mannitol
1 ml of trace elements solution/liter of broth Seventy five ml portions of this medium were prepared, inoculated and incubated in 500 ml Erlenmeyer flasks as in Example 1. Two such flasks (140 ml) of heavy growth were used to inoculate 10 liters of sterile medium in a 14 liter fermentor. Incubation was at 29° C, with air flow at 2 liters per minute, agitation at 750 RPM, and atmospheric pressure. The pH was controlled at 7.2–8.0. With these conditions, the dissolved oxygen reached a minimum of 84% of saturation 22 hours after inoculation. The carbon dioxide content of the exhaust gas was highest at this time, viz. 2.3 volume percent. At 39 hours, the dissolved oxygen was at 98% saturation and the exhaust gas $CO_2$ had declined to 1.4%. The pigment content was determined by uv absorption.

Five hundred ml of a sterile ten fold concentrate of this medium was fed to the fermentor over a 9–10 hour period beginning at 39¼ hours. By the 44th hour, the dissolved oxygen had declined to 86% of saturation, and the exhaust gas $CO_2$ content was 2.75 volume percent, indicating an increase in metabolic activity. After addition of this medium, one liter of a sterile 10% mannitol solution was added over a sixteen-hour period.

Eighty seven hours after inoculation the pigment content of 8(R), 9(R), 10(S), 10a(R)-tetrahydro-9,10,10a,11-tetrahydroxy-3,8-dimethyl-1-propyl-6aH(S)-pyrano[2″,3″:5′, 4′]furo[2′,3′:5,6]azuleno-[2,3-c]pyridine-5,13-dione, was determined by uv adsorption.

A total of 175 ml of 1N sodium hydroxide was used for pH control during this experiment. No acid was required.

EXAMPLE 3

A butanol extract of the broth filtrate prepared in Example 1 was concentrated to dryness under reduced pressure. The residue (236.4 g) which contained 40.67 g of the dione by UV assay, was extracted with methanol (3 liters) and filtered. To the filtrate 890 g of silica gel (0.2 – 0.5 mm) were added and the solvent removed at reduced pressure. The resulting solid was charged on a column containing 3 kg of silica gel. Chloroform containing increasing amounts of methanol (0 – 25%) was used as eluant. Fractions of 11 liter were taken and three main pools were made. The first (8.6 g) was a mixture of the dione and pigment B (compound III above). The second (31.6 g) and third (18.7 g) contained the dione 8(R), 9(R), 10(S), 10a(R)-tetrahydro-9,10,10a,11-tetrahydroxy-3,8-dimethyl-1-propyl-6aH(S)-pyrano[2'',3'':5',4']furo[2',3':5,6]azuleno-[2,3-c]Pyridine-5,13-dione in purities of 84% and 79% resp. determined by UV assay.

The first pool was rechromatographed on neutral polystyrene resin. Using water with increasing amounts of methanol (0 - 100%) as eluant, 945 mg of pigment B was isolated as an amorphous red solid: $\lambda_{max}^{H_2O}(\epsilon)$ 218 (18000), 273 (21300), 333 (8600), 412 (6700), 520 (5200) nm; ir (KBr) 3400 (broad), 1720, 1650, 1590, 1580 cm$^-$.

In the same way a 10 g portion of the dione 8(R),9(R),10(S),10a(R)-tetrahydro-9,10,10a,11-tetrahydroxy-3,8-dimethyl-1-propyl-6aH(S)-pyrano [2'',3'':5',4']furo[2'3':5 6]azuleno-[2,3-c]pyridine-5,13-dione was further purified to yield 3.7 g of pure material and several other slightly contaminated fractions with a purity above 90%. This dione exhibited the following physical chemical properties $\lambda_{max}$ $^{H_2O}(\epsilon)$ 216 (18800), 275 (31500), 300 (infl. 9600), 325/8 (sh. 800), 400 (sh. 7300), 421/2 (9500), 523 (8600) nm; ir (KBr) 3400 (broad), 1704, 1635, 1577, 1560 nm $^{-1}$; $\delta^{DMSO\,(d_6)}$ 1.00 (t, 3, J = 7 Hz, CH$_3$—CH$_2$); 1.16 (d, 3, J = 7 Hz, CH$_3$—CH); 1.72 (m,2,CH$_3$ — CH$_2$); 2.54 (s,3, CH$_3$—Ar); 3.04 (t, 2, J = Hz, CH$_2$ —Ar); 3.53 (s, 1, CH); 3.82 (q, 1, J =7 Hz, CH$_3$—CH); 3.98 (s, 1, CH); 5.20 (s, 1 CH); 6.52 (s, 1, CH); 8.21 (s, 1, CH; $[\alpha]_D^{25}$ −937.50 (c 0.2, H$_2$O).

EXAMPLE 4

To a solution of 4.0 g of the dione isolated in Example 3 in 200 ml of absolute methanol and 400 ml of acetone, 10 g of molecular sieves and 2 ml of concentrated aqueous sulfuric acid were added and the reaction mixture heated to reflux for 2 hours. The molecular sieves were removed by filtration and 8 g of anhydrous sodium acetate were added to the filtrate. After removing the solvent, the residue was dissolved in chloroform, washed with water, dried (Na$_2$SO$_4$), filtered and concentrated giving 3.6 g of crude 8(R),9(R),10(S),10a(R)-tetrahydro-10a, 11-dihydroxy-9,10-(isopropylidenedioxy)-3,8-dimethyl-1-propyl-6aH(S)-pyrano[2'',3'':5',4']-furo[2',3':5,6]azuleno[2,3-c]-pyridine-5,13-dione as product.

Further purification of this isopropylidene derivative was carried out by chromatography on silica gel using CHCl$_3$/EtOH 9:1 to give the pure isopropylidene product 8(R),9(R),10(S),10a(R)-tetrahydro-10a,11-dihydroxy-9,10-(isopropylidenedioxy)-3,8-dimethyl-1-propyl-6aH(S)-pyrano[2'',3'':5',4']furo[2',3':5,6-]azuleno[2,3-c]-pyridine-5,13-dione.

EXAMPLE 5

To a solution of 1.5 g of isopropylidene product of Example 4 in 120 ml of chloroform, 1.5 ml of benzoyl chloride was added. After stirring at room temperature for 16 hours a second portion of 0.5 ml of benzoyl chloride was added and stirring continued for 24 hours. After the addition of 1 g of potassium carbonate and stirring for an additional 4 hours, the reaction mixture was filtered, the filtrate concentrated under reduced pressure and the residue chromatographed on silica gel. Chloroform/ethanol 9:1 eluted 1.12 g of 10a-benzoyloxy-8(R),9(R),10(S),10a(R)-tetrahydro-11-hydroxy-9,10-(isopropylidenedioxy)-3,8-dimethyl-1-propyl-6aH(S)-pyrano[2'',3'':5',4', ]furo[2',3':5,6]-azuleno[2,3-c]pyridine-5,13-dione.

EXAMPLE 6

To a solution of 511 mg of 10a-benzoyloxy-8(R),9(R),10(S),10a(R)-tetrahydro-11-hydroxy-9,10-(isopropylidenedioxy)-3,8-dimethyl-1-propyl-6aH(S)-pyrano[2'',3'':5',4']furo[2',3':5,6]-azuleno[2,3-c]pyridine-5,13-dione /in 30 ml of chloroform, 0.1 ml of pyridine and 0.1 ml of benzoyl chloride were added. The reaction mixture changed instantaneously from purple to orangebrown. After stirring for one half hour at room temperature, solvents were removed under reduced pressure and the residue was chromatographed on magnesium silicate. Chloroform/diethyl ether 1:1 parts by volume eluted 75 mg of 10a,11-bis(benzoyloxy)-8(R),9(R),10(S),10a(R)-tetrahydro-9,10-(isopropylidenedioxy)-3,8-dimethyl-1-propyl-6aH(S)-pyrano[2'',3'':5',4']furo[2', 3':5,6]-azuleno[2,3-c]pyridine-5,13-dione (yellow) and 107 mg of 5,10a-b is(benzoyloxy)-8(R),9(R),10(S), 10a(R)-tetrahydro-9,10-(isopropylidenedioxy)-3,8-dimethyl-1-propyl-6aH(S)-pyrano[2'',3'':5',4']furo[2',3':5,6]-azuleno[2,3-c]pyridine-11,13 -dione (orange) as oils. The same compounds were obtained using potassium carbonate as base in refluxing chloroform.

EXAMPLE 7

To 100 mg of the isopropylidene derivative product of Example 4 dissolved in 2 ml of methanol, an ethereal solution of diazomethane (1.2 eq.) was added at room temperature. After stirring for 2½ hours, a second portion of diazomethane (1 eq.) was added and the reaction mixture stirred overnight. The solvents were then removed at reduced pressure and the residue chromatographed on silica gel using CHCl$_3$/ether 1:1 parts by volume to give 75 mg of a yellow compound. Upon addition of ethanol 15 mg of 8(R),9(R),10(S),10a(R)-tetrahydro-10a-hydroxy-9,10-(isopropylidenedioxy)-5-methoxy-3,8-dimethyl-1-propyl-6aH(S)-pyrano[2'',3'':5',4']furo-[2',3':5,6]azuleno[2,3-c]pyridine-11,13-dione crystallized, mp. 185°–7°,$[\alpha]_D^{25}$ + 150.2° (c 0.78, CHCl$_3$).

EXAMPLE 8

To a solution of 1.5 g of the isopropylidene derivative of Example 4 in 150 ml of chloroform, 1.5 g of silver oxide and 15 ml of methyl iodide were added and the reaction mixture heated under anhydrous conditions to 40°. After 1½ hours a second portion of 6 ml of methyl iodide and 1 g of silver oxide were added. After a total reaction time of 3 hours, the reaction mixture was filtered through diatomaceous earth, the filtrate concentrated and then the methyl ethers formed separated by chromatography on silica gel. Chloroform containing up to 50% ether eluted 1.0 g of 8(R),9(R),10(S),10a(R)-tetrahydro-10a-hydroxy-9,10-(isopropylidenedioxy)-5-methoxy-3,8-dimethyl-1-propyl-6aH(S)-pyrano[2'',3'':5',4']furo-[2',3':5,6]azuleno[2,3-c]pyridine-11,13-dione, recrystallized from EtOH; yellow crystals mp. 185°–7°, no depression of mixed melting point with the compound obtained by the diazomethane reaction of Example 7; and 280 mg of a second methyl ether, 8(R),9(R),10(S),10a(R)-tetrahydro-10a-hydroxy-9. 10-(isopropylidenedioxy)-11-methoxy-3,8-dimethyl-1-propyl-6aH(S)-pyrano[2',3'':5',4']-furo[2',3':5,6-]azuleno[2,3-c]pyridine-5,13-dione, recrystallized from methylene chloride/n-hexane, orange crystals mp. 150°-2°, $[\alpha]_D^{25}$ − 122°, (c 0.261, CHCl$_3$).

EXAMPLE 9

A solution of 300 mg of 10a-benzoyloxy-8(R),9(R),10(S), 10a (R)-tetrahydro-11-hydroxy-9,10-(isopropylidenedioxy)-3,8-dimethyl--propyl-6aH (S)-pyrano [2",3":5', 4']furo[2',3': 5,6]azuleno[2,3-c]pyridine-5,13-dione in 15 ml of 90% trifluoroacetic acid and 30 ml of water was stirred at room temperature for 3 hours. The reaction mixture was stripped down and chromatographed on silica gel. Chloroform with 15% ethanol eluted 307 mg of 10a benzoyl-8(R),9(R), 10(S),10a(R)-tetrahydro-9,10,11-trihydroxy-3,8-dimethyl-1-propyl-6aH (S)-pyrano-[2",3":5', 4']furo[2',3':5,6]-azuleno[2,3-c]-pyridine-5,13-dione contaminated with silica gel. The compound was, therefore, dissolved in 1 ml of ethanol and filtered through a small milipore filter (syringe type) and the filtrate concentrated and dried to an amorphous red solid.

EXAMPLE 10

To a solution of 500 mg of the isopropylidene derivative of Example 5, in 200 ml of chloroform, 300 mg of p-bromobenzyl bromide and 500 mg silver oxide were added. The reaction mixture was stirred at room temperature for 15 hours, another 150 mg of p-bromobenzyl bromide was added, and stirring continued for 24 hours. The reaction mixture was filtered over diatomaceous earth, the filtrate concentrated and the two ethers separated by chromatography on silica gel. Methylene chloride/ether 3:1 eluted 345 mg of 5-(4-bromobenzyloxy)-8(R), 9(R),10(S),10a(R)-tetrahydro-10a-hydroxy-9,10-(isopropylidene-dioxy)-3,8-dimethyl-1-propyl-6aH(S)-pyrano-[2",3":5',4']furo[2',3':5,6]-azuleno[2,3-c]-pyridine-11,13-dione, which was recrystallized from a mixture of toluene and petroleum ether; yellow crystals mp. 184°-5°, $[\alpha]_D^{25}$ + 124.9°(c 0.932, CHCl$_3$).

EXAMPLE 11

To a solution of 500 mg of the isopropylidene derivative of Example 4, in 150 ml of chloroform, 400 mg of o-bromobenzoyl chloride was added and stirred for 72 hours at room temperature. An additional 200 mg of o-bromobenzoyl chloride was added and stirring continued for 40 hours. Solvent was removed under reduced pressure and the residue redissolved in chloroform and charged on a column containing 120 g of silica gel in chloroform. After elution with 300 ml of chloroform, the column was eluted with chloroform/methanol (9:1) and the fractions containing the product (TLC) were combined and concentrated to dryness under reduced pressure. To remove some o-bromobenzoic acid that was present, the residue was redissolved in chloroform and washed with 50 ml of saturated sodium bicarbonate solution, water and dried (Na$_2$SO$_4$). The organic layer was concentrated to dryness and the residue crystallized from ethanol. Recrystallization from ethanol gave 10a-(2-bromobenzoyloxy)-8(R), 9(R), 10(S), 10a(R)-tetrahydro-11-hydroxy-9,10-(isopropylidenedioxy)-3,8-dimethyl-1-propyl-6aH(S)-pyrano[2",3":5',4']furo[2',3':5,6]azuleno [2,3-c]pyridine-5,13-dione as red crystals; mp 192 dec.

EXAMPLE 12

To a solution of 310 mg of 10a-(2-bromobenzoyloxy)-8(R),9(R),10(S), 10a(R)-tetrahydro-11-hydroxy-9,10-(isopopylidenedioxy)-3,8-dimethyl-1-propyl-6aH(S)-pyrano[2",3":5',4']-furo[2',3':5,6]azuleno[2,3-c]pyridine-5,13-dione in 120 ml of chloroform, 3 ml of methyl iodide and 400 mg of silver oxide were added and the mixture stirred overnight at room temperature. An additional 2 ml of methyl iodide and 200 mg of silver oxide were added and stirring continued for 4 hours. Filtration separated the solid material and the filtrate was concentrated to dryness under reduced pressure. The residue was dissolved in a small amount of chloroform, charged on a silica gel column and eluted with a mixture of chloroform/ether (9:1 parts by volume). Fractions were collected and pooled based on TLC. The first pooled material gave 98 mg of a yellow solid 10a-(2-bromobenzoyloxy)-8(R),9(R),10(S),10a(R)-tetrahydro-9,10-(isopropylidenedioxy)-5-methoxy-3,8-dimethyl-1-propyl-6aH(S)-pyrano[2",3":5',4']-furo[2',3':5,6]azuleno[2,3-c]pyridine-11,13-dione. The second pooled fraction gave 24 mg of 10a-(2-bromobenzoyloxy)-8(R),9(R),10(S),10a(R)-tetrahydro-9,10-(isopropylidenedioxy)-11-methoxy-3,8-dimethyl-1-propyl-6aH(S)-pyrano [2",3":5',4']-furo[2',3':5,6]azuleno[2,3-c]pyridine-5,13-dione which crystallized from ethanol as orange crystals, mp 210–14 dec.

EXAMPLE 13

To a solution of 500 mg of the isopropylidene derivative of Example 4, 780 mg of p-bromobenzoyl chloride was added. After stirring at room temperature for 48 hours a second portion of 280 mg of p-bromobenzoyl chloride was added and after 24 hours, a third portion (78 mg). The reaction mixture was concentrated after 48 hours and the residue chromatographed on silica gel. Chloroform/ethanol 9:1 parts by volume eluted 400 mg of 10a-(4-bromobenzoyloxy)-8(R),9(R),10(S), 10a(R)-tetrahydro-11-hydroxy-9,10-(isopropylidenedioxy)-3,8-dimethyl-1-propyl-6aH(S)-pyrano[2",3":5',4']-furo[2',3':5,6]azuleno[2,3-c]pyridine-5,14-dione as an amorphous red solid.

EXAMPLE 14

To a solution of 300 mg of 10a-(4-bromobenzoyloxy)-8(R),9(R),10(S), 10a(R)-tetrahydro-11-hydroxy-9,10-(isopropylidenedioxy)-3,8-dimethyl-1-propyl-6aH(S)-pyrano[2",3":5',4']-furo[2',3':5,6]azuleno[2,3-c]pyridine-5,13-dione in 120 ml of chloroform, 300 mg of silver oxide and 3 ml of methyl iodide were added. The reaction mixture was stirred at room temperature for 7 hours and filtered over diatomaceous earth. The filtrate was concentrated and the two methyl ethers separated by chromatography on silica gel. Methylene chloride/ether eluted 195 mg of 10a-(4-bromobenzoyloxy)-8(R),9(R),10(S),10a(R)-tetrahydro-9,10-(isopropylidenedioxy)-5-methoxy-3,8-dimethyl-1-propyl-6aH(S)-pyrano[2",3":5',4']-furo[2',3':5,6]azuleno[2,3-c]pyridine-11,13-dione, which was crystallized from diisopropyl ether as yellow crystals: mp. 135°-6°; and 56 mg of 10a-(4-bromobenzoyloxy)-8(R),9(R),10(S),10a(R)-tetrahydro-9,10-(isopropylidenedioxy)-11-methoxy-3,8-dimethyl-1-propyl-6aH(S)-pyrano[2",3":5'4']-furo[2',3':5,6]azuleno[2,3-c]pyridine-5,13-dione, crystallized from diisopropyl ether as orange crystals, mp. 218°-220°.

EXAMPLE 15

To a solution of 300 mg of Pigment B prepared in Example 3 in 10 ml of methanol and 40 ml of acetone, 0.1 ml of concentrated aqueous sulfuric acid was added

17 as well as 2 ml of 2,2-dimethoxypropane. The reaction mixture was refluxed for 1½ hours and another 2 ml portion of 2,2-dimethoxypropane was added. After 30 minutes, 500 mg of anhydrous sodium acetate was added to the cooled reaction mixture and the solvent as removed at reduced pressure. The residue was dissolved in chloroform and washed with water, dried (Na$_2$SO$_4$), filtered and concentrated. The reaction product was purified by chromatography on silica gel. Chloroform/ethanol 9:1 parts by volume eluted 210 mg of isopropylidene derivative of pigment B, a red solid; ir (KBr) 1710, 1630, 1580 cm$^{-1}$; $\lambda_{max}^{EtOH}$ ( $\epsilon$ ) 217/8 (19000), 277 (26900), 300 (sh. 10700), 328 (8600), 342/3 (sh. 8200), 395 (sh. 6900), 413 (9000), 537/8 (7400) nm; M$^+$ m/e 481 (calcd. for C$_{26}$H$_{27}$NO$_8$—481).

EXAMPLE 16

By the procedure of Example 13, the isopropylidene derivative of Example 4 is reacted with meta-bromobenzoyl chloride to produce 10a-(3-bromobenzoyloxy)-8(R), 9(R), 10(S), 10a(R)-tetrahydro-11-hydroxy-9,10-(isopropylidenedioxy)-3,8-dimethyl-1-propyl-6aH(S)-pyrano[2″,3″:5′,4′]-furo[2′3′:5,6]azuleno[2,3-c]pyridine-5,13-dione which is converted by the procedure of Example 14 to 10a-(3-bromobenzoyloxy)-8(R) 9(R), 10(S),10a(R)-tetrahydro-9,10-(isopropylidenedioxy)-5-methoxy-3,8-dimethyl-1-propyl-6aH(S)-pyrano[2″,3″:5′,4′]-furo[2′,3′:5,6]azuleno[2,3-c]pyridine-11,13-dione and 10a-(3-bromobenzoyloxy)-8(R),9(R),10(S),10a(R)-tetrahydro-9,10-(isopropylidenedioxy)-11-methoxy-3,8-dimethyl-1-propyl-6aH(S)-pyrano[2″,3″:5′,4′]-furo[2′,3′:5,6]azuleno [2,3-c]pyridine-5,13-dione.

EXAMPLE 17

By the procedure of Example 13, the isopropylidene derivative of Example 4 is reacted with para-bromoorthonitrobenzoyl chloride to produce 10a-(4-bromo-2-nitrobenzoyloxy)-8(R),9(R),10(S),10a(R)-tetrahydro-11-hydroxy-9,10-(isopropylidenedioxy)-3,8-dimethyl-1-propyl-6aH(S)-pyrano[2″,3″:5′,4′]furo[2′,3′:5,6]azuleno[2,3-c]pyridine-5,13-dione which is converted by the procedure of Example 14 to 10a-(4-bromo-2-nitrobenzoyloxy)-8(R),9(R),10(S),10a(R)-tetrahydro-9,10-(isopropylidenedioxy)-5-methoxy-3,8-dimethyl-1-propyl-6aH(S) pyrano-[2″,3″:5′,4′]furo[2′,3′:5,6]azuleno[2,80c]-pyridine-11,13-dione and 10a-(4-bromo-2-nitrobenzoyloxy)-8(R),9(R),10(S),10a(R)-tetrahydro-9,10-(isopropylidenedioxy)-11-methoxy-3,8-dimethyl-1-propyl-6aH(S)-pyrano-[2″,3″:5′,4′]furo[2′,3′:5,6]azuleno[2,3-c]-pyridine-5,13-dione.

EXAMPLE 18

By the procedure of Example 13, the isopropylidene derivative of Example 4 is reacted with 3,5-dibromobenzoyl chloride to produce 10a-(3,5-dibromobenzoyloxy)-8(R),9(R),10(S),10a(R)-tetrahydro-11-hydroxy-9,10-(isopropylidenedioxy)-3,8-dimethyl-1-propyl-6aH(S)-pyrano[2″,3″:5′,4′]-furo[2′,3′:5,6]azuleno[2,3-c]pyridine-5,13-dione which is converted by the procedure of Example 14 to 10a-(3,5-dibromobenzoyloxy)-8(R),9(R),10(S),10a(R)-tetrahydro-9,10-(isopropylidenedioxy)-5-methoxy-3,8-dimethyl-1-propyl-6aH(S)-pyrano[2″,3″:5′,4′]furo-[2′,3′:5,6]azuleno[2,3-c]pyridine-11,13-dione and 10a-(3,5-dibomobenzoyloxy)-8(R),9(R),10(S),10a(R),-tetrahydro-9,10-(isopropylidenedioxy-11-methoxy-3,8-dimethyl-1-propyl-6aH(S)-pyrano[2″,3″:5′,4′]-furo[2′,3′:5,6]azuleno[2,3-c]pyridine-5,13-dione.

EXAMPLE 19

By the procedure of Example 13, the isopropylidene derivative of Example 4 is reacted with 2-bromo-3-nitrobenzoyl chloride to produce 10a-(2-bromo-3-nitrobenzoyloxy)-8(R),9(R),10(S),10a(R)-tetrahydro-11-hydroxy-9,10-(isopropylidenedioxy)-3,8-dimethyl-1-propyl-6aH(S)-pyrano[2″,3″:5′,4′]furo[2′,3′:5,6]-azuleno[2,3-c]pyridine-5,13-dione.

EXAMPLE 20

To a solution of 500 mg of the dione isolated in Example 3 in 200 ml of absolute methanol and 30 ml of cyclohexanone, 2g of molecular sieves and 0.5ml of concentrated aqueous sulfuric acid were added and the reaction mixture heated to reflux for 2 hours. The molecular sieves were removed by filtration and 8 g of anhydrous sodium acetate were added to the filtrate. After removing the solvent, the residue was dissolved in chloroform, washed with water, dried (Na$_2$SO$_4$), filtered and concentrated giving the cyclohexylidene derivative as product.

Further purification of this derivative was carried out by chromatography on silica gel using CHCl$_3$/EtOH 9:1 parts by volume to give the pure product 9,1-0-(cyclohexylidenedioxy)-8(R),9(R),10(S),10a(R)-tetrahydro-10a,11-dihydroxy-3,8-dimethyl-1-propyl-6aH(S)-pyrano[2″,3″:5′,4′]furo[2′,3′:5,6]-azuleno[2,3-c]pyridine-5,13-dione as an amorphous red solid.

EXAMPLE 21

A Kood-Aid type of beverage was formulated as follows

|  | g/100 ml. |
|---|---|
| citric acid | 0.1 |
| malic acid | 0.05 |
| adipic acid | 0.05 |
| Na phosphate (Monobasic H$_2$O) | 0.01 |
| Dione of Example 3 | 0.005 |
| Sucrose | 10.0 |
| H$_2$O | 100 ml |

This drink had the same color and color stability as a drink prepared from the above ingredients except that F, D and C Red 2 was substituted for the dione of Example 3.

EXAMPLE 22

The formulated Kool-Aid type of beverage drink used for the evaluation of the pigment contained the following ingredients:

|  | g/100 ml |
|---|---|
| Citric acid | 0.1 |
| Malic acid | 0.05 |
| Adipic acid | 0.05 |
| Na phosphate (monobasic H$_2$O) | 0.01 |
| Sucrose | 10.0 |
| Color (Compound III) | 0.005 |
| H$_2$O | 100 ml |

This drink had same properties as the drink prepared in Example 21.

We claim:

1. A coloring agent having the tautomeric formulae:

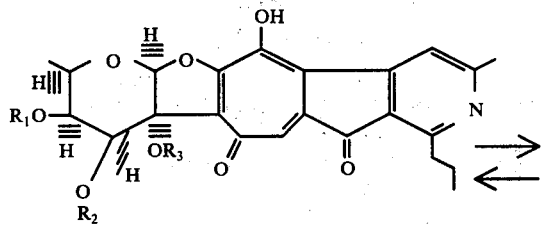

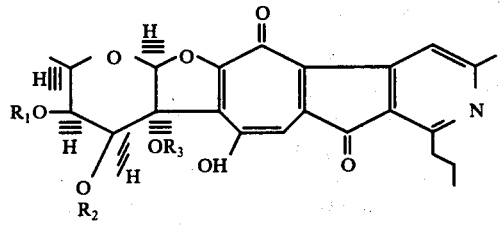

wherein $R_1$ and $R_2$ are individually hydrogen or taken together form

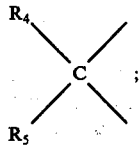

$R_3$ is hydrogen or

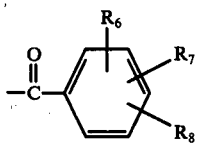

$R_4$ and $R_5$ are lower alkyl or taken together with attached carbon atoms forms cycloalkyl from 3 to 8 carbon atoms; and $R_6$, $R_7$ and $R_8$ are hydrogen, halogen or nitro.

2. The compound of claim 1 wherein $R_1$, $R_2$ and $R_3$ are hydrogen.

3. The compound of claim 1 wherein $R_1$ and $R_2$ are isopropylidene.

4. The compound of claim 3 wherein $R_3$ is

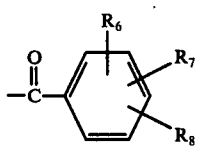

wherein $R_6$, $R_7$ and $R_8$ are as above.

5. The compound of claim 4 wherein $R_6$, $R_7$ and $R_8$ are hydrogen.

6. The compound of claim 4 wherein $R_6$ is hydrogen, $R_7$ is nitro and $R_8$ is bromo.

7. A compound of the formula

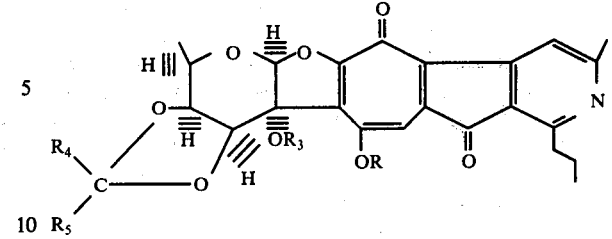

wherein $R_4$ and $R_5$ are lower alkyl or taken together with attached carbon atoms form cycloalkyl from 3 to 8 carbon atoms;

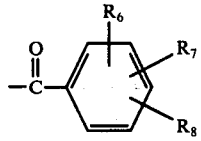

R is lower alkyl,

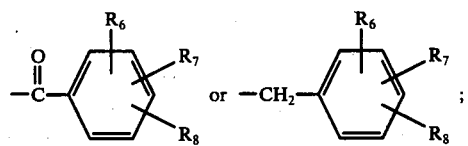

$R_6$, $R_7$ and $R_8$ are hydrogen, halogen or nitro; with the proviso that when R is

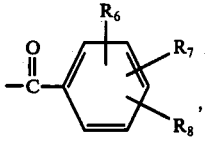

$R_3$ is other than hydrogen.

8. The compound of claim 7 wherein said compound is 10a-(4-bromobenzoyloxy)-8(R),9(R),10(S),10a(R)-tetrahydro-9,10-(isopropylidenedioxy)-11-methoxy-3,8-dimethyl-1-propyl-6aH(S)-pyrano[2'',3'':5',4']-furo[2',3':5,6]azuleno[2,3-c]pyridine-5,13-dione.

9. The compound of claim 7 wherein said compound is 10a-(4-bromo-3-nitrobenzoyloxy)-8(R),9(R),10(S),10a(R)-tetrahydro-9,10-(isopropylidenedioxy)-5-methoxy-3,8-dimethyl-1-propyl-6aH(S)-pyrano[2'',3'':5',4']furo[2',3':5,6]azuleno[2,3-c]pyridine-11,13-dione.

10. The compound of claim 7 wherein said compound is 11-(4-bromobenzyloxy)-8(R),9(R),10(S),10a(R)-tetrahydro-10a-hydroxy-9,10-(isopropylidenedioxy)-3,8-dimethyl-1-propyl-6aH(S)-pyrano[2'',3'':5',4']-furo[2',3':5,6]azuleno[2,3-c]pyridine-5,13-dione.

11. The compound of the formula

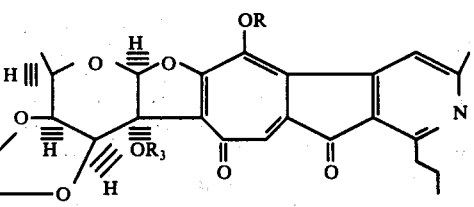

wherein $R_4$ and $R_5$ are lower alkyl or taken together with attached carbon atoms form cycloalkyl from 3 to 8 carbon atoms;

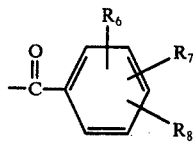

R is lower alkyl,

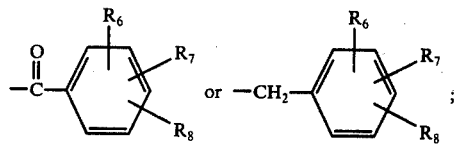

$R_6$, $R_7$ and $R_8$ are hydrogen, halogen or nitro; with the proviso that when R is

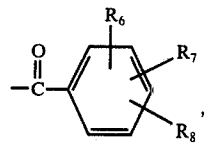

$R_3$ is other than hydrogen.

12. The compound of claim 11 wherein said compound is 10a-(2-bromobenzoyloxy)-8(R),9(R),10(S),10a(R)-tetrahydro-11-hydroxy-9,10-(isopropylidenedioxy)-3,8-dimethyl-1-propyl-6aH(S)-pyrano[2",3":5',4']furo[2',3':5,6]azuleno[2,3-c]pyridine-5,13-dione.

13. The compound of claim 11 wherein said compound is 5-(4-bromobenzyloxy)-8(R),9(R),10(S),10a(R)-tetrahydro-10a-hydroxy-9,10-(isopropylidenedioxy)-3,8-dimethyl-1-propyl-6aH(S)-pyrano[2",3":5',4']-furo[2',3':5,6]azuleno[2,3-c]pyridine-11,13-dione.

14. The compound of claim 11 wherein said compound is 5,10a-bis(benzoyloxy)-8(R),9(R),10(S),10a(R)-tetrahydro-9,10-(isopropylidenedioxy)-3,8-dimethyl-1-propyl-6aH(S)-pyrano[2",3":5',4']furo[2',3':5,6]-azuleno[2,3-c]pyridine-11,13-dione.

* * * * *